(12) United States Patent
Yang et al.

(10) Patent No.: US 9,056,097 B2
(45) Date of Patent: Jun. 16, 2015

(54) COMPOSITE OF AMORPHOUS CALCIUM PHOSPHATE/CALCIUM SULFATE HEMIHYDRATE (CSH/ACP) FOR BONE IMPLANTATION AND PROCESS FOR PRODUCING THE SAME

(75) Inventors: Jen-Chang Yang, Taipei (TW);
Sheng-Yang Lee, Taipei (TW);
Duen-Cheng Wang, Taipei (TW);
Haw-Ming Huang, Taipei (TW);
Wei-Jen Chang, Taipei (TW); Malosi Poma, Taipei (TW); Hong-Da Wu, Taipei (TW); Dian-Yu Ji, Taipei (TW)

(73) Assignee: Taipei Medical University, Taipei (TW)

(*) Notice: Subject to any disclaimer, the term of this patent is extended or adjusted under 35 U.S.C. 154(b) by 161 days.

(21) Appl. No.: 13/010,473

(22) Filed: Jan. 20, 2011

(65) Prior Publication Data
US 2012/0189683 A1    Jul. 26, 2012

(51) Int. Cl.
*A61K 33/42* (2006.01)
*A61L 27/42* (2006.01)

(52) U.S. Cl.
CPC ............ *A61K 33/42* (2013.01); *A61L 27/425* (2013.01); *A61L 27/427* (2013.01)

(58) Field of Classification Search
CPC .. B65D 63/1018; A61K 33/42; A61L 27/425; A61L 27/427
See application file for complete search history.

(56) References Cited

U.S. PATENT DOCUMENTS

| | | | |
|---|---|---|---|
| 7,351,280 B2* | 4/2008 | Khairoun et al. ............ 106/690 |
| 7,670,419 B2 | 3/2010 | Bohner | |
| 7,700,066 B1 | 4/2010 | Yang et al. | |
| 2002/0183417 A1 | 12/2002 | Shimp | |
| 2005/0119746 A1 | 6/2005 | Lidgren | |
| 2007/0026030 A1* | 2/2007 | Gill et al. ...................... 424/423 |
| 2008/0014242 A1 | 1/2008 | Overby et al. | |

FOREIGN PATENT DOCUMENTS

CH    WO 2005084726    *   9/2005    .............. A61L 24/02

OTHER PUBLICATIONS

Nillson et al. (J Mater Sci: Materials in Medicine 2003, 14, 399-404).*
Nilsson et al. Nilsson et al. (J Biomed Mater Res 2002;61:600-607).*
A Novel Resorbable Composite of Calcium Sulfate and Amorphous Calcium Phosphate Bone Substitute for Dental Implants, Abstract of Master Thesis of Malosi Poma (English abstract provided), published on line on Jul. 21, 2010.
Kawai T, Murakami S, Hiranuma H, Sakuda M.: "Healing after removal of benign cysts and tumors of the jaws. A radiologic appraisal," Oral Surg Oral Med Oral Pathol Oral Radiol Endod 1995; 79(4): 517-25.
Kawai T, Murakami S, Hiranuma H, Sakuda M.: "Radiographic changes during bone healing after mandibular fractures," Br J Oral Maxillofac Surg 1997; 35(5): 312-8.
(Continued)

*Primary Examiner* — Ernst V Arnold
(74) *Attorney, Agent, or Firm* — McDonnell Boehnen Hulbert & Berghoff LLP (57) ABSTRACT

The invention provides a composite of α-calcium sulfate (CS) hemihydrate/amorphous calcium phosphate (α-CSH/ACP), comprising α-CSH and ACP at a weight ratio of about 10:90 to about 90:10. Particularly, the composite of the invention has a resorption period of 3-6 months. The invention also provides a one-pot process for producing α-CSH/ACP composite of the invention. The one-pot process of the invention can produce α-CSH and ACP in a single process and easily obtain α-CSH/ACP composite.

16 Claims, 8 Drawing Sheets

(56) References Cited

OTHER PUBLICATIONS

Urban RM, Turner TM, Hall DJ, Inoue N, Gitelis S.: "Increased bone formation using calcium sulfate-calcium phosphate composite graft," Clin Orthop Relat Res 2007;459:110-7.

Nilsson M, Wang JS, Wielanek L, Tanner KE, Lidgren L.: "Biodegradation and biocompatability of a calcium sulphate-hydroxyapatite bone substitute," J Bone Joint Surg 2004;86(1):120-125.

Osteoset(R) T, Medicated Bone Graft Substitute, Technical Monograph, Wright Medical Technologies, Inc., 2006, pp. 1-15.

* cited by examiner

COMPOSITE OF AMORPHOUS CALCIUM PHOSPHATE/CALCIUM SULFATE HEMIHYDRATE (CSH/ACP) FOR BONE IMPLANTATION AND PROCESS FOR PRODUCING THE SAME

FIELD OF THE INVENTION

The invention provides a composite of α-calcium sulfate (CS) hemihydrate/amorphous calcium phosphate (α-CSH/ACP) and a process for production thereof. Particularly, the composite of the invention comprises α-CSH and ACP at a weight ratio of about 10:90 to about 90:10.

BACKGROUND OF THE INVENTION

Due to concerns over potential immune response and supply shortages associated with autografts and allografts, synthetic bone graft substitutes (SBGSs) for augmenting the bone have rapidly gained popularity in the field of implantation. SBGSs are widely used in implantation due to their biocompatibility, osteoconduction, and minimal risk of disease transmission. Typical ceramic bone graft materials such as hydroxyapatite (HA, $Ca_{10}(PO_4)_6(OH)_2$), β-tricalcium phosphate (β-TCP, $β-Ca_3(PO_4)_2$) and calcium sulfate (CS, $CaSO_4$), can be presented in different product forms such as powder, granule, pellet, putty, or block to apply to various bone damage conditions. At present, many fabrication methods for bone grafts have been developed, as summarized in Table 1.

TABLE 1

| Product name (producer, factory) | Composition (content) | Comments (phase) |
|---|---|---|
| Healos (Depuy Spine) | | Sponge |
| ProOsteon (Interpore Int., USA) Previous name: Replam Hydroxyapatite-Porites or RHAP | | Particulate or block brittle. Radiopaore size 190-230 μm) 500: Porites Gonipora (large pores) R: Resorbcity impedes assessment of healing. Slow resorption R-form |
| Collagraft (Zimmer Inc, USA) | HA coated 70% Type I bovine collagen | Granules and strips require augmentation with aspirated marrow |
| MBCP (Biomatlante) | Replaniform coralline macroporous HA 200: Porites (pable | Granules, rectangular sticks, cylinders or wedges |
| Triosite (Zimmer Europe Ltd, UK) | 60% HA, 40% TCP | Also called MBCP (macroporous biphasic calcium phosphate) or BCP |
| BCP (Bioland) | 60% HA, 40% TCP | |
| Ostilit (Stryker Howmedica Osteonics, UK) | 20% HA, 80% TCP, without macroporous | Granules and blocks for nonstructural grafts |
| BoneSave (Stryker Howmedica Osteonics, UK) | 20% HA, 80% TCP, pore size: 400-600 μm | Granules, stronger than Ostilit, for use as a void filler and in grafting |
| Cerasorb ORTHO (curasan) | Pure phase β-TCP, micropores: <80 μm | Granular size being 500-1,000 μm or 1,000-2,000 μm |
| Vitoss ™ Scaffold (curasan) | β-TCP, micropores: <1-1000 μm | Morsel (1-4 mm sizes) and blocks (9 × 23 mm cylinder) |
| Conduit ™ TCP Granules (DePuy Spine) | >99% (β-TCP) $Ca_3(PO_4)_2$, pore: 1-600 μm | Irregular shaped granules having an average diameter between 1.5 and 3 mm |
| Cellplex ™ TCP synthetic cancellous bone (Wright) | Porous calcium phosphate made from TCP, pore size: 100-400 μm | |
| Ceros 82 | β-TCP, porosity varies to adjust resorption between 6 and 12 months | Lower compressive strength than Ceros 80 |
| Synthes (USA) chronOS ™ (Synthes) | β-TCP pore size: 100-500 μm | Granules, blocks, wedge and cylinders |
| Calciresorb (Ceraver Osteal, France) | Porous TCP | Periodontal applications |
| Synthograf (Milter, USA) | Small size and dense TCP | Periodontal applications |
| Augmen (Milter, USA) | Large size and dense TCP | Periodontal applications |
| Skelite ™ (Millenium Biologix) | Multiphase, porous calcium phosphate | Granules and blocks |
| Norian Skeletal Repair System (SRS) | Self-setting calcium phosphate cement | Injectable cement, augmentation of fracture |

There is great demand in the field of implementation surgery for an ideal SBGS. The in vivo resorption rate is one vital property of SBGSs that can be improved. SBGSs for implants should be rapidly resorbable and replaced by new bone so that implants can be placed as early as possible in the augmented site. However, the ideal resorption period for SBGS use in implants (especially in dentistry) is still uncertain. Clinical studies have reported that a stress-free healing period of 3-6 months is prerequisite to implant osseointegration. For example, a 3-6-month healing period was proposed by Kawai et al. in their radiographic studies of healing of jawbone defects and fractures (Kawai T, Murakami S, Hiranuma H, Sakuda M. Healing after removal of benign cysts and tumors of the jaws. A radiologic appraisal. Oral Surg Oral Med Oral Pathol Oral Radiol Endod 1995; 79(4): 517-25; Kawai T, Murakami S, Hiranuma H, Sakuda M. Radiographic changes during bone healing after mandibular fractures. Br J Oral Maxillofac Surg 1997; 35(5): 312-8). It was suggested that at a natural healing rate, most jawbone defects required an average time of 3-6 months to heal.

Calcium sulfate (CS) is a rapidly resorbable and biocompatible bone substitute with a bone regeneration effect and angiogenic effect. Depending on the amount of crystal water, calcium sulfate can be classified as calcium sulfate dihydrate ($CaSO_4.2H_2O$, i.e., gypsum), calcium sulfate hemihydrate ($CaSO_4.0.5H_2O$, i.e., plaster of Paris) or calcium sulfate anhydrite ($CaSO_4$). The following are the chemical reaction formulae of the above reactions:

Dehydration: $CaSO_4.2H_2O(s)+heat \rightarrow CaSO_4.$
$\frac{1}{2}H_2O(s)+1\frac{1}{2}H_2O$ $CaSO_4.\frac{1}{2}H_2O(s)+heat \rightarrow CaSO_4+2H_2O$ Hydration: $CaSO_4.\frac{1}{2}H_2O(s)+3/2H_2O \rightarrow CaSO_4.$
$2H_2O(s)$ The in vivo resorption period of calcium sulfate hemihydrate is longer than that of calcium sulfate dihydrate. However, calcium sulfate hemihydrate will transform into calcium sulfate dihydrate through hydration. Therefore, in commercial processes for producing tablet calcium sulfate bone substitute, water is added to calcium sulfate hemihydrate to form tablet calcium sulfate dihydrate and then the tablet calcium sulfate dihydrate is transformed into calcium sulfate hemihydrate by dehydration. CS is associated with many other biomaterials. In vitro studies of the attachment of osteoblast cells to CS and the resorption of CS by osteoclasts have been reported. However the high in vivo resorption rate of CS of 1-2 months is considered too rapid, as it can limit bone regeneration and cause serous drainage in some clinical applications.

It has been recommended that merging CS with a less-resorbable calcium phosphate compound would be better for human applications. Many studies have worked on combining CS with other calcium phosphates like HAp, β-tricalcium phosphate (β-TCP), and α-tricalcium phosphate (α-TCP) (Urban R M, Turner T M, Hall D J, Inoue N, Gitelis S. Increased bone formation using calcium sulfate-calcium phosphate composite graft. Clin Orthop Mat Res 2007; 459: 110-7; Nilsson M, Wang J S, Wielanek L, Tanner K E, Lidgren L. Biodegradation and biocompatability of a calcium sulphate-hydroxyapatite bone substitute. J Bone Joint Surg 2004; 86(1):120-125). US Publication No. 20050119746 provides an artificial bone mineral substitute material comprising at least one ceramic and at least one water soluble non-ionic X-ray contrast agent and illustrates an embodiment comprising 1-30% calcium sulfate hemihydrate and 50-99% α-TCP. However, their resorption rates were far too slow.

Amorphous calcium phosphate (ACP; with an approximate compositional formula of $Ca_3(PO_4)_2.0.8H_2O$) is a non-crystalline and the most soluble form of tricalcium phosphate. It is usually treated in vivo as a precursor of biological bone apatite during bone formation. In vitro, ACP is the first phase that precipitates from a supersaturated solution prepared by rapidly mixing solutions containing calcium and phosphate ions. The composition and poor crystalline structure of ACP mimic natural bone apatite, and would be a better bone substitute than highly crystalline hydroxyapatite (HAp). Previous studies confirmed that ACP shows better bioactivity than HAp, because greater adhesion, proliferation, and differentiation of osteogenic cells were observed on ACP substrates than crystalline HAp substrates. However, ACP will transform to Hap with longer resorption rate after contacting water through phase transformation.

U.S. Pat. No. 7,351,280 relates to a composition and method for producing interconnective macroporous, resorbable and injectable calcium phosphate-based cements (MICPCs), which provide a self-setting calcium phosphate cement (CPC). The invention of the patent adds carbonate, magnesium, zinc, fluoride and pyrophosphate ions to stabilize ACP. U.S. Pat. No. 7,670,419 discloses a hydraulic cement based on calcium phosphate for surgical use comprising A) a first component comprising powder particles of calcium phosphate; and B) a second component comprising water. The invention of the patent uses ACP that is preheated to 500° C. and then milled to shorten time of hydrating and hardening CPC. US Publication No. 20020183417 relates to a calcium phosphate bone graft material, to a process for making the calcium phosphate bone graft material, and to an osteoimplant fabricated from the calcium phosphate bone graft material. The invention uses plasma spray to coat ACP on the surface of Hap to form a new bone substitute. US Publication No. 20080014242 discloses a synthetic bone substitute material suitable for use as a replacement for cancellous bone in a bone graft composition, the material comprising a reticulated framework of interconnecting bioceramic struts defining an interconnecting interstitial void volume, and a solid non-porous composition substantially filling the interstitial void volume and in intimate contact with the reticulated framework, the pore-filling composition comprising calcium sulfate. However, the bone substitutes provided in the above prior art cannot provide satisfactory resorption rate.

Therefore, there remains a need in the art for improved bone substitute materials providing resorption rate suitably parallel to the natural healing rate of the human bone.

SUMMARY OF THE INVENTION

The invention provides a composite of α-calcium sulfate hemihydrate/amorphous calcium phosphate (α-CSH/ACP), which comprises α-CSH and ACP at a weight ratio of about 10:90 to about 90:10.

The invention also provides a process for producing α-CSH/ACP composite, which comprises the following steps:
(a) separately dissolving a calcium ion-containing solution and a sulfate ion-containing solution in calcium chloride solutions;
(b) heating the solutions of (a) to a temperature of about 80° C. to 100° C.; and mixing the two solutions for reaction to produce α-calcium sulfate hemihydrate (α-CSH);
(c) filtrating the resulting solution of (b) to separate α-CSH solid from the solution;

(d) adding a phosphate compound to the solution in (c) to react with calcium chloride in (a) to obtain amorphous calcium phosphate (ACP); and (e) mixing α-CSH of (c) and ACP of (d) and then adding water to produce a composite of α-calcium sulfate hemihydrate and amorphous calcium phosphate (α-CSH/ACP).

DETAILED DESCRIPTION OF THE INVENTION

The invention develops a resorbable composite of α-calcium sulfate (CS) hemihydrate/amorphous calcium phosphate (α-CSH/ACP) for use as bone graft substitute, and a one-pot process for manufacture of a resorbable bone graft substitute of α-calcium sulfate (CS) hemihydrate/amorphous calcium phosphate (α-CSH/ACP). Unexpectedly, the α-CSH/ACP composite of the invention provides a resorption period of 3-6 months that is specifically suitable for dental implantation surgery. Moreover, the one-pot process of the invention can produce α-CSH and ACP in a single process and easily obtain α-CSH/ACP composite.

In one aspect, the invention provides a composite of α-calcium sulfate hemihydrate/amorphous calcium phosphate (α-CSH/ACP), which comprises α-CSH and ACP at a weight ratio of about 10:90 to about 90:10. In one embodiment, the α-CSH is α-CaSO$_4$.0.5H$_2$O. In another embodiment of the invention, the α-CSH and ACP is at a weight ratio of about 10:90, about 20:80, about 30:70, about 40:60, about 50:50, about 60:40, about 70:30, about 80:20 or about 90:10. In a further embodiment of the invention, the -CSH/ACP of the invention is in granular form, powder form or paste form.

According to the invention, the natural healing rate of the human bone should parallel the ideal resorption rate of synthetic bone graft substitute (SBGS) for implants. The invention unexpectedly found that α-CSH and ACP at a specific ratio will generate hydration by adding water, whereas α-CSH and ACP will not transform into calcium sulfate dehydrate (CSD) and Hap, which needs longer time for resorption respectively. The invention combines α-CSH with ACP to create a biocompatible SBGS that could be resorbed and substituted by bone within a 3-6-month period, and this resulting α-CSH/ACP composite can mimic the natural bone regeneration rate with a 3-6 month period. Preferably, the natural bone is jaw bone, so the composite of the invention is especially suitable for dental implantation.

According to the invention, the addition of ACP to CS improves the osteoconductivity of the composite by reducing the resorption rate and mimicking the natural bone structure and mineral components. The α-CSH/ACP bone substitutes of the invention were biocompatible, osteoconductive, and resorbable with a mathematically estimated resorption period of about 3-6 months. The novel composite CSH/ACP of the invention can shorten the implant healing and treatment periods. The matching of resorption rates of synthetic bone graft substitutes (SBGS) with the healing rate for extraction sockets is highly desirable for implants. Therefore, the composite of the invention is an ideal SBGS for implants.

In another aspect, the invention provides a process for producing α-CSH/ACP composite, which comprises the following steps:

(a) separately dissolving a calcium ion-containing solution and a sulfate ion-containing solution in calcium chloride solutions;

(b) heating the solutions of (a) to a temperature of about 80° C. to 100° C.; and mixing the two solutions for reaction to produce α-calcium sulfate hemihydrate (α-CSH);

(c) filtrating the resulting solution of (b) to separate α-CSH solid from the solution;

(d) adding a phosphate compound to the solution in (c) to react with calcium chloride in (a) to obtain amorphous calcium phosphate (ACP); and (e) mixing α-CSH of (c) and ACP of (d) and then adding water to produce a composite of α-calcium sulfate hemihydrate and amorphous calcium phosphate (α-CSH/ACP).

The invention provides a one-pot process for producing the α-CSH/ACP composite of the invention. The process of the invention can produce α-CSH and ACP simultaneously and obtain the α-CSH/ACP composite by mixing the resulting α-CSH and ACP. Briefly, the above reactions can be accomplished in a one-pot process and α-CSH, ACP and α-CSH/ACP can be easily produced through the one-pot process.

According to the invention, in step (a) of the process, a calcium ion-containing solution and a sulfate ion-containing solution are separately solved in calcium chloride solutions. In an embodiment of the invention, the calcium ion-containing solution is, but is not limited to, a solution containing calcium chloride, calcium hydroxide, calcium nitrate or calcium oxide. Preferably, the calcium ion-containing solution is calcium nitrate solution. In another embodiment of the invention, the sulfate ion-containing solution is, but is not limited to, a solution containing potassium sulfate or sulfuric acid. According to the invention, the calcium chloride in the process is used as crystallization catalyst to insure that the crystal phase of calcium sulfate hemihydrate produced in step (b) will not transform into calcium sulfate dihydrate.

According to the invention, in step (b) of the process, the solutions of (a) are heated to a temperature higher than 80° C. and then mixed for reaction to produce α-calcium sulfate hemihydrate (α-CSH). Preferably, the solutions are heated to a temperature of 95° C. According one embodiment of the invention, the reaction time is at least 2 hours.

According to the invention, in step (c) of the process, the resulting solution of (b) is subjected to filtration to separate α-CSH solid from the solution, whereby α-CSH and liquid part can be obtained respectively.

According to the invention, in step (d) of the process, a phosphate compound is added to the solution in (c) so that it reacts with calcium chloride in (a) to obtain amorphous calcium phosphate (ACP). In an embodiment of the invention, the phosphate compound is, but is not limited to, sodium dihydrogen phosphate (Na$_2$HPO$_3$), potassium dihydrogen phosphate ($K_2HPO_3$) or phosphoric acid ($H_3PO4$). Preferably, the phosphate compound is sodium dihydrogen phosphate. In another embodiment of the invention, the reaction is performed at a basic pH. Preferably, the pH value ranges from 7.5 to 10.0.

According to the invention, in step (e) of the process, α-CSH of (c) and ACP of (d) are mixed to form a mixture. Subsequently, water is added to the mixture to produce a composite of α-calcium sulfate hemihydrate and amorphous calcium phosphate (α-CSH/ACP). In one embodiment of the invention, the α-CSH and ACP is mixed at a weight ratio of about 10:90 about 90:10. According to the invention, the addition of water to the mixture of α-CSH and ACP will generate hydration reaction to produce and harden the composite of α-CSH/ACP. In one embodiment of the invention, the α-CSH and ACP are mixed at a specific ratio range to have desired resorption period. Preferably, the α-CSH is α-$CaSO_4$.$0.5H_2O$. In another embodiment, the weight ratio of α-CSH and ACP is about 60:40. Preferably, the α-CSH/ACP composite of the invention provides a resorption period of 3-6 months.

EXAMPLES

Example 1

Preparation of α-CSH/ACP Composite of the Invention

Preparation of α-CSH

Figure 1:
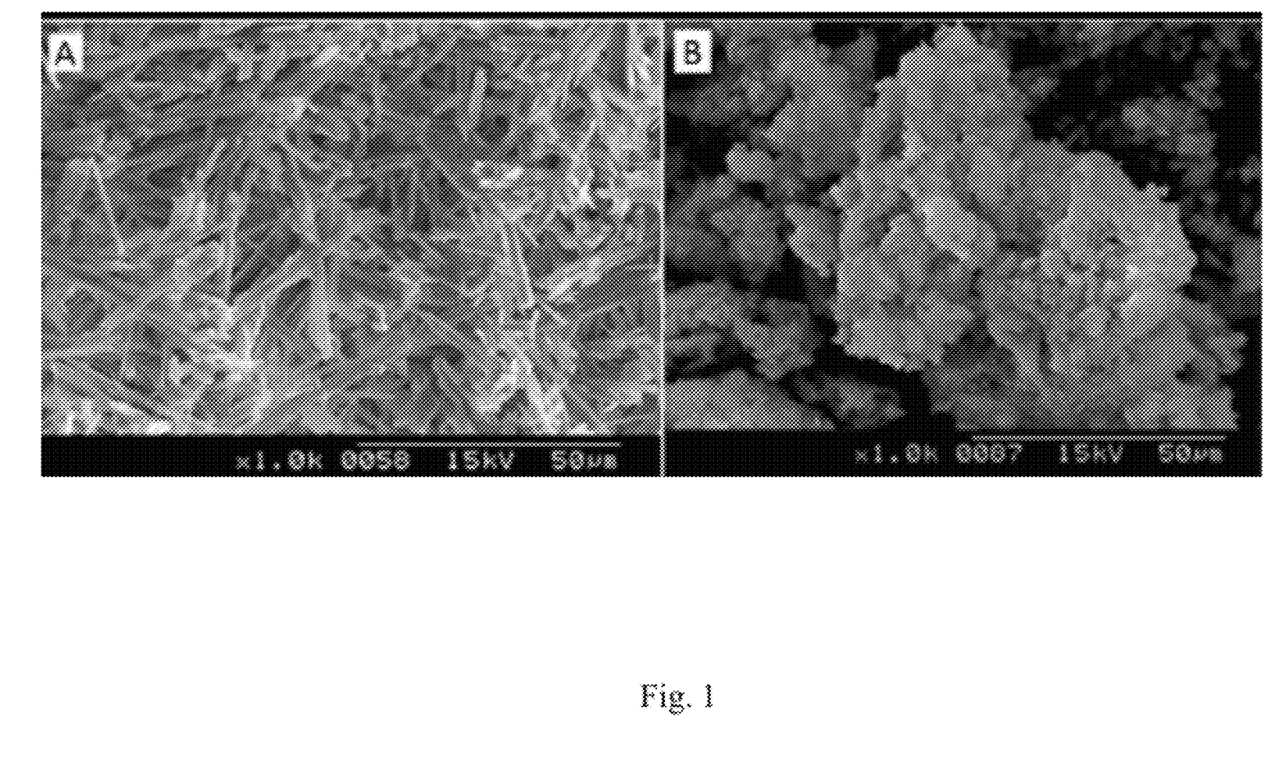
FIG. 1(a) shows the SEM graph of α-CSH.
FIG. 1(b) shows the SEM graph of ACP.
FIG. 1(c) shows the X-ray diffraction (XRD) pattern of α-CSH and ACP.
FIG. 1(d) shows the DSC thermogram of α-CSH.

Pure α-CSH was prepared by a wet precipitation method using calcium chloride ($CaCl_2$) as a crystallization catalyst. Calcium nitrate ($Ca(NO_3)_2 4H_2O$) of 0.1 mole and 0.1 M potassium sulfate ($K_2SO_4$) were separately dissolved in 50 ml of a 3.5 M $CaCl_2$ solution. Both solutions were preheated to 95° C.; then they were mixed and incubated at atmospheric pressure for 2 h. The detailed procedures are reported in U.S. Pat. No. 7,700,066. The crystalline phase of the harvested α-CSH was identified by x-ray diffraction (XRD), differential scanning calorimetric (DSC), and scanning electron microscopy (SEM) analysis. The crystal morphology of the α-CSH was examined by SEM and is shown in FIG. 1a. The texture of CS revealed relatively thin, long, needle-type crystals that interlocked with each other. Additionally, XRD analysis shown in FIG. 1c displayed typical 2-theta (θ) values of the peaks at 14.75°, 25.71°, 29.76°, and 31.91° associated with the crystal planes of (110), (310), (220), and (−114), indicating the character of α-CSH. The DSC thermogram (FIG. 1d) showed an endothermic peak at approximately 210° C. and a small exothermic peak at 230° C. demonstrating the characteristics of α-CSH.

Preparation of ACP

A buffering medium at pH 9 was prepared by the addition of sodium hydroxide (NaOH) into 100 ml of distilled water. The preparation of ACP was conducted by rapidly adding 100 ml of a sodium phosphate dibasic (J.T. Baker, ST, USA) aqueous solution (2.33 M) and 100 ml of a $CaCl_2$ solution (3.50 M) to the buffering medium. The envisaged ACP was filtered by high-power filtration (Sibata, Circulating Aspirator WJ-20, Tokyo, Japan) and stored in a freezer. It was freeze-dried for 2 days, then its crystalline structure was confirmed by XRD analysis. The XRD pattern of the calcium phosphate prepared by the wet precipitation method disclosed a broad peak characteristic for the amorphous structure (FIG. 10. SEM photographs in FIG. 1b display flaky particles of ACP.

Figure 2:
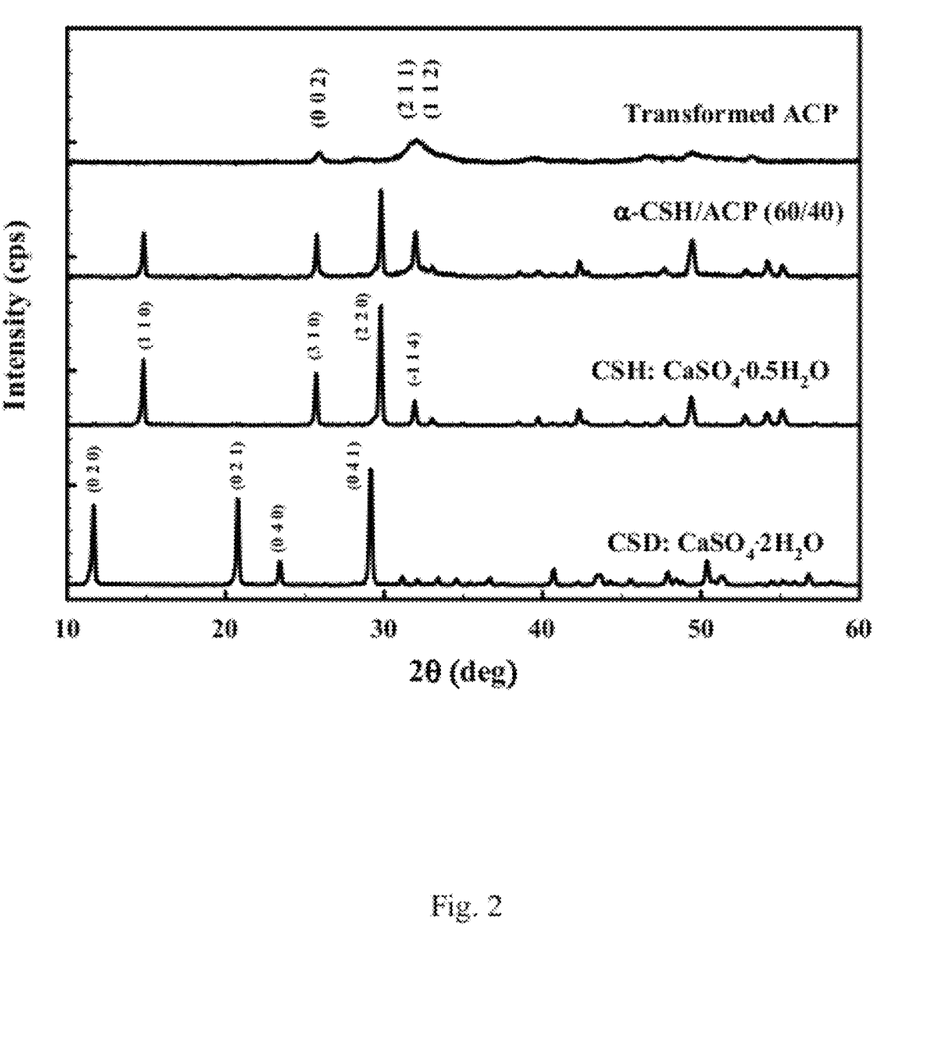
FIG. 2 shows X-ray diffraction (XRD) pattern of transformed ACP, α-CSH/ACP, CSH and CSD.
Figure 3:
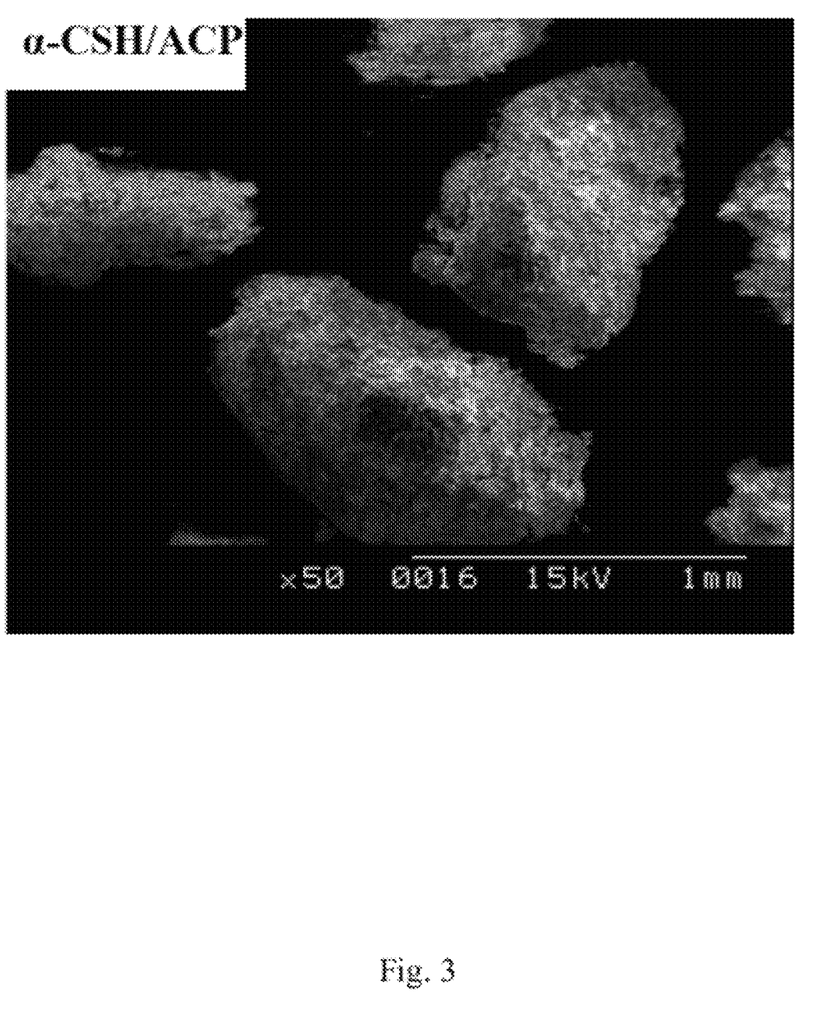
FIG. 3 shows the SEM graph of α-CSH/ACP of the invention.

Preparation of α-CSH/ACP (60/40) Granules

α-CSH and ACP were mixed together (in a 60:40 weight ratio) with deionized water at a powder to liquid ratio of 10:6. The composite was then allowed to set at room temperature before being dried in an oven at 80° C. Using a pestle, the material was ground in a grinding bowl and sieved to isolate particles of 500-840 µm. After mixing α-CSH with water at a powder-to-liquid ratio of 10:6 for 24 h, XRD analysis revealed complete transformation of α-CSH to new diffraction peaks located at 11.64°, 20.75°, 23.41°, and 29.14° correlated with the characteristic crystal planes of (020), (021), (040) and (041) for CSD after the hydration reaction. In contrast, when α-CSH/ACP (60/40) was mixed with water overnight, the hydrated composite displayed XRD diffraction peaks for CSH only located at 14.75°, 25.66°, 29.76°, and 31.91° which were associated with the crystal planes of (110), (310), (220), and (−114) with no detectable peaks indicating the phase transformation to CSD (FIG. 2). FIG. 3 shows the SEM of the α-CSH/ACP (60/40).

Example 2

In Vitro Dissolution Test of α-CSH/ACP

Figure 4:
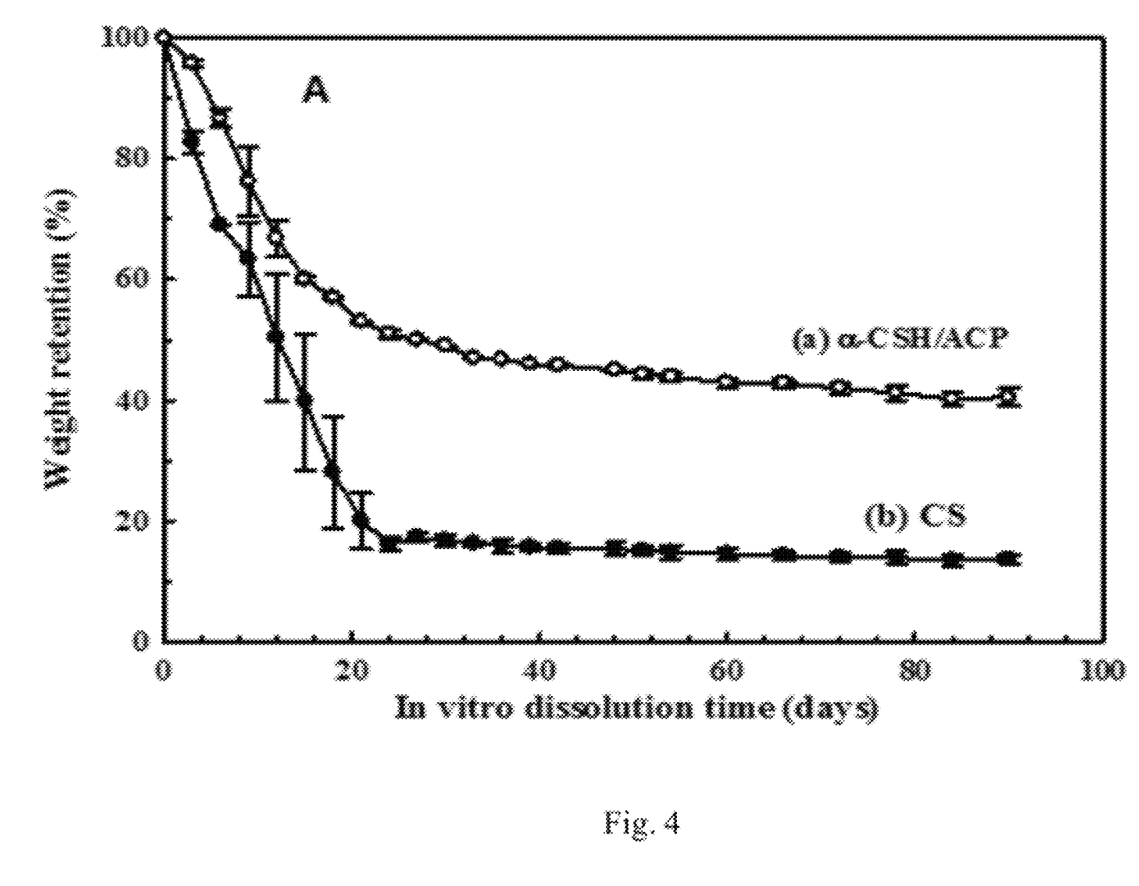
FIG. 4(a) shows the graph of the dissolution test for calcium sulfate (CS) alone and composite α-CSH/ACP (60/40) in PBS.
FIG. 4(b) shows XRD diagram of CS and α-CSH/ACP residues after the dissolution test in PBS.

In vitro dissolution tests are essential to demonstrate equivalence in dissolution behavior for resorbable biomaterials in clinical use. α-CSH/ACP (60/40) and CS weighing 1 g for each test material were prepared. Samples were placed in plastic tea bags, put in polyethylene tubes, and weighed to an accuracy of 0.01 mg. Subsequently 50 ml of phosphate-buffered solution (PBS) were added to each tube and incubated in a shaking bath (B603D, FIRSTREK, ST, USA) at 37° C. and shaken at a speed of 30 rpm. After 3 days, the polythene tubes were centrifuged (Hermle, Z 323 K, United Corps, Germany), and the PBS was carefully removed. Samples were washed with 30 ml of deionized water, dried, and cooled before their new weight was recorded. Another 50 ml of fresh PBS was added, and the samples were added to the shaking bath for another 3 days. Dissolution rates of samples were measured by calculating the percentages of sample weight retention. The experiment was discontinued after 3 months when insignificant percentage weight loss was detected. FIG. 4a reveals the weight-retention profiles for α-CSH/ACP (60/40) and CS at various time periods up to 90 days in PBS. Both α-CSH/ACP (60/40) and CS displayed rapid dissolution in the first 20 days, followed by a remarkably slow dissolution rate to reach weight retention plateaus of around 13.5%±0.7% and 40.5%±1.4%, respectively. XRD analysis of the residual from the in vitro dissolution test (FIG. 4b) revealed a characteristic pattern of poor crystalline HAp for both specimens, but there were no detectable peaks indicating the existence of CSs. This indicates that both CS and α-CSH/ACP (60/40) composites were transformed to poor crystalline HAp after dissolution in PBS.

Example 3

Animal Study

Eight beagles (1 year old) were used in this experiment. These dogs were bred and raised in Ping Tung National University of Science and Technology. Animal selection, management, and surgical procedures were approved by the Animal Care and Use Committee of Taipei Medical University. General and local anesthesia were performed by an intramuscular injection of 0.1 mg/kg of atropine (Tai-Yu Co., Hsinchu, Taiwan) and 6-12 mg/kg of Zoletil/Virbac 50 (Virbac Laboratories, France), respectively. Local anesthesia was performed by injection of lidocaine/epinephrine (Ora Inj. cartridge, 2% lidocaine hydrochloride and epinephrine 1:73,000, Showa Yakuhin-Kako, Japan). Extraction of the bilateral mandibular first molars, and second, third, and fourth premolars (M1 and P2-P4) was performed in all dogs, and the wounds were allowed to heal for 3 months. Postoperatively, the dogs were given ampicillin for an anti-inflammatory effect. Defects of 5- and 8-mm depths were created by a trephine bur on both sides of the mandible. Bone defects were filled with α-CSH/ACP (60/40), Osteoset® (CS, Wright Medical Technology, Arlington, Tenn., USA), and an empty defect was used as a control. Samples (n=4) were harvested after 3 and 6 weeks. At each harvesting time point, a trephine bur (6 mm in diameter) was used to collect the specimens, which were immediately placed in 10% formalin. The sectioned samples were stained using hematoxylin and eosin. Sections were examined for evidence of biocompatibility and bone regeneration under a light microscope. The percentage area of new bone formation was calculated using the ImageJ 1.37c software (National Institutes of Health (NIH), Bethesda, Md., USA). The difference of percentage areas of new bone formed between the treated defects and the control defect were tested with an unpaired Student's t-test. A p value of <0.05 indicated statistical significance.

Figure 5:
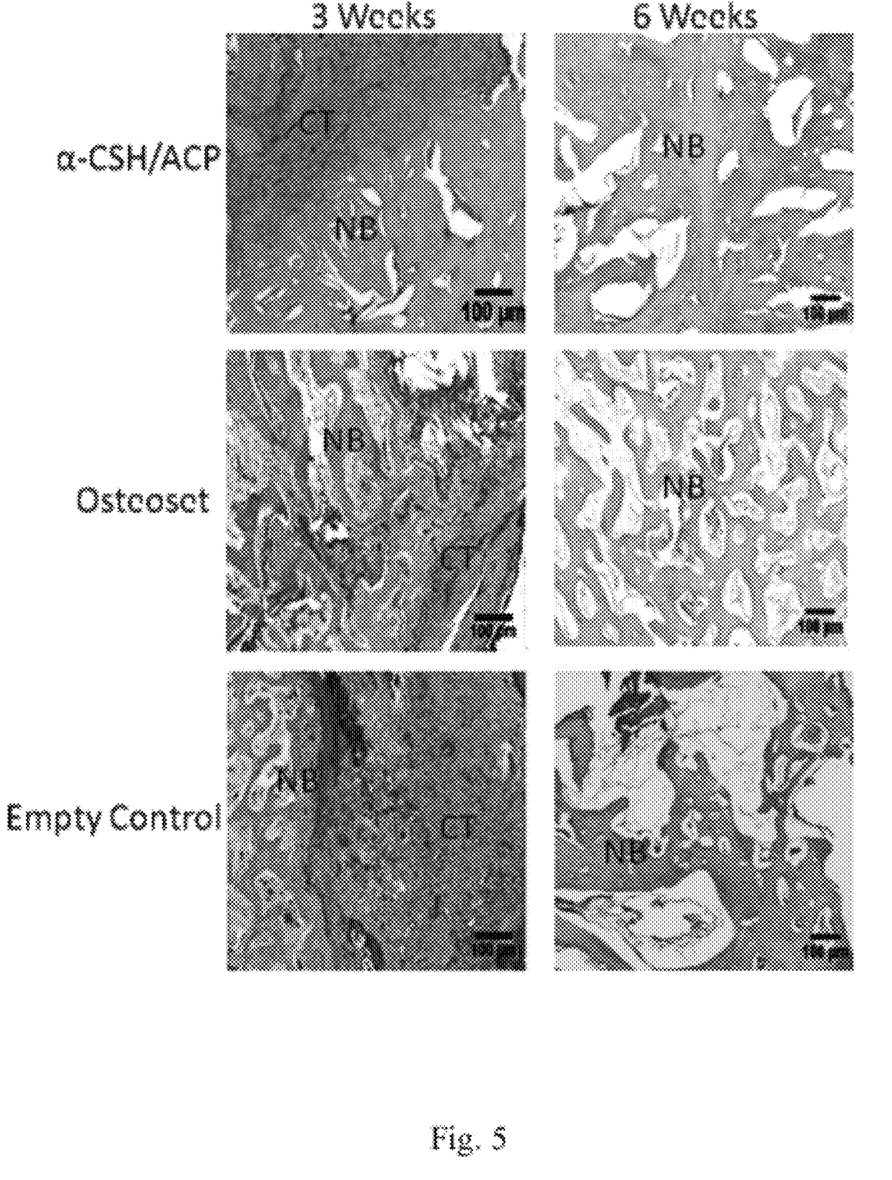
FIG. 5 shows the histological micrographs of bone defects filled with α-CSH/ACP (60/40), Osteoset® and an empty defect (Original magnification of 20× for all images; CT, connective tissue; NB, new bone).

FIG. 5 shows that the empty control group was dominated by connective tissue. In the Osteoset® and α-CSH/ACP groups, both of which showed obvious bone formation after 3 weeks, some connective tissue still existed in both groups. Six weeks postoperatively, no fibrous tissues or inflammatory cells were detected. Some new bone was observed in the empty control group, but numerous unhealed cavities were observed. In the Osteoset® and α-CSH/ACP (60/40) groups, the new bone that formed was very notable, but there were more unhealed cavities in the Osteoset® group than in the α-CSH/ACP (60/40) group. The exact area of new bone formation was estimated by a histomorphometric method in the following experiment.

Example 4

Histomorphometry Assay (Quantitative Evaluation)

New bone formation was quantified by image analysis; the results are summarized in table 1. At 3 weeks, the ratio of new bone formation for defects treated with α-CSH/ACP (60/40) (21.1%±15.0%) was significantly higher than that of the empty control (13.6%±9.5%) (p<0.05), but there was no significant difference in the amount of new bone formation between defects grafted with Osteoset® (29.0%±16.0%). Thus, filling defects with α-CSH/ACP or Osteoset® enhanced bone regeneration rates within 3 weeks. Six weeks postoperatively, more bone had formed in defects treated with α-CSH/ACP (60/40) (62.2%±6.8%) than Osteoset® (53.3%±4.6%) (p<0.01) and the empty control (40.1%±7.2%) (p<0.0002). The above results demonstrate the α-CSH/ACP (60/40) groups showed better performance; for this reason, adding ACP to CS enhanced the performance of bone regeneration, especially in the middle stage of healing.

Finally, the linear least squares fitting technique was used to estimate the complete healing period for bone defects in the canine model treated with α-CSH/ACP (60/40) bone substitutes.

Figure 6:
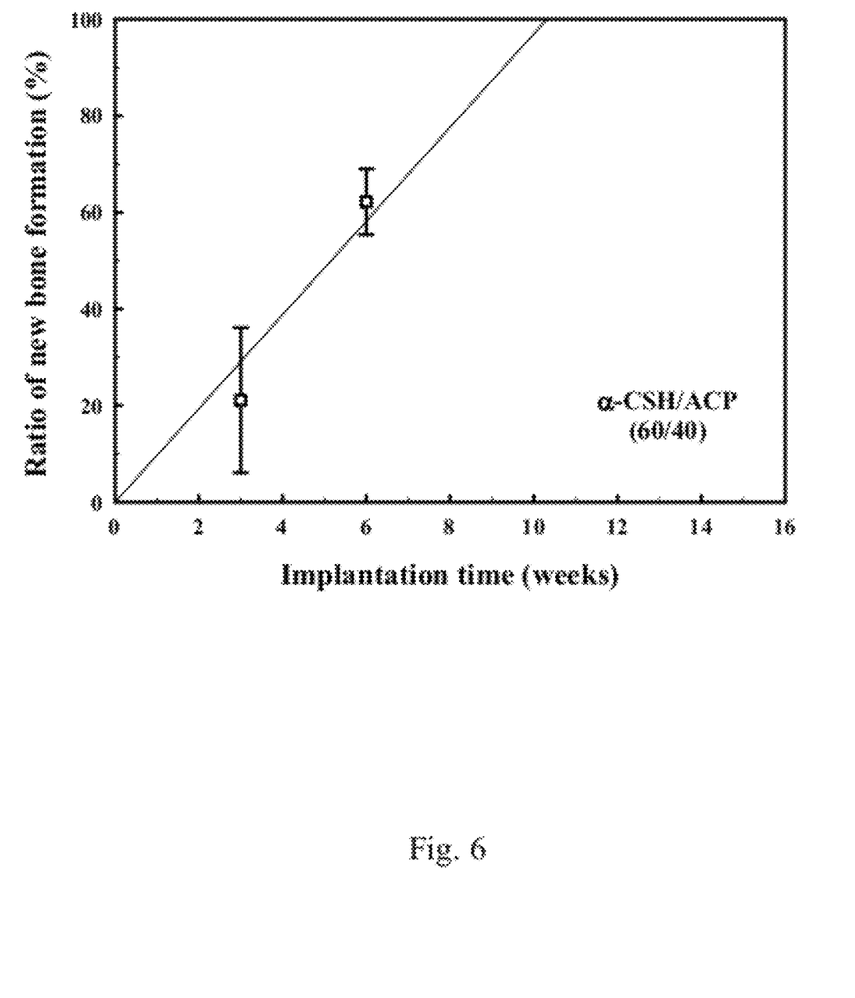
FIG. 6 shows extrapolation graph of the complete healing period for bone defects in the canine model treated with α-CSH/ACP (60/40) bone substitutes.

The extrapolation graph (FIG. 6) approximated that the complete healing period for the α-CSH/ACP (60/40) bone substitute would be within a range of 10-12 weeks (10.3 weeks). The usual canine model has a bone regeneration rate 1.5-2 times faster than humans, so the 10-12-week healing period in our study may be equivalent 15-18 weeks (3.75-4.5 months) in humans.

TABLE 1

| Groups | New bone formations (%) | |
|---|---|---|
| | 3 weeks (SD) | 6 weeks (SD) |
| α-CSH/ACP | 21.1 (15.0) * | 62.2 (6.8) *** |
| Osteoset ® | 29.0 (16.0) * | 53.3 (4.6) * |
| Empty Control | 13.6 (9.5) | 40.1 (7.2) |

What is claimed is:

1. A composite of α-calcium sulfate (CS) hemihydrate/amorphous calcium phosphate (α-CSH/ACP), which comprises α-CSH and ACP at a weight ratio of about 40:60 to about 70:30.

2. The composite of claim 1, wherein the α-CSH is α-CaSO$_4$. 0.5H$_2$O.

3. The composite of claim 1, wherein the α-CSH and ACP is at a weight ratio of about 40:60, about 50:50, about 60:40, or about 70:30.

4. The composite of claim 1, which is in granular form.

5. The composite of claim 1, which is in powder form.

6. The composite of claim 1, where is in paste form.

7. A process for producing α-CSH/ACP composite, which comprises the following steps:
   (a) separately dissolving a calcium ion-containing solution and a sulfate ion containing solution in calcium chloride solutions;
   (b) heating the solutions of (a) to a temperature of about 80° C. to 100° C.; and mixing the two solutions for reaction to produce α-calcium sulfate hemihydrate (α-CSH);
   (c) filtrating the resulting solution of (b) to separate α-CSH solid from the solution;
   (d) adding a phosphate compound to the solution in (c) to react with calcium chloride in (a) to obtain amorphous calcium phosphate (ACP); and
   (e) mixing α-CSH of (c) and ACP of (d) and then adding water to produce a composite of α-calcium sulfate hemihydrate and amorphous calcium phosphate (α-CSH/ACP) at a α-CSH/ACP weight ratio of about 40:60 to about 70:30.

8. The process of claim 7, wherein the calcium ion-containing solution is a solution containing calcium chloride, calcium hydroxide, calcium nitrate or calcium oxide.

9. The process of claim 7, wherein the calcium ion-containing solution is calcium nitrate solution.

10. The process of claim 7, wherein the sulfate ion-containing solution is a solution containing potassium sulfate or sulfuric acid.

11. The process of claim 7, wherein in step (d), the phosphate compound is sodium dihydrogen phosphate (Na$_2$HPO$_3$), potassium dihydrogen phosphate (K$_2$HPO$_3$) or phosphoric acid (H$_3$PO4).

12. The process of claim 7, wherein in step (d), the phosphate compound is sodium dihydrogen phosphate.

13. The process of claim 7, wherein the reaction in step (d) is performed at a basic pH.

14. The process of claim 13, wherein the pH value ranges from 7.5 to 10.0.

15. The process of claim 7, wherein the weight ratio of α-CSH and ACP is about 40:60, about 50:50, about 60:40, or about 70:30.

16. The process of claim 7, wherein in step (e), the α-CSH is α-CaSO$_4$.0.5H$_2$O.

* * * * *